United States Patent [19]
Weisman et al.

[11] 4,012,796
[45] Mar. 22, 1977

[54] INTERPOSITIONING COLLAR FOR PROSTHETIC BONE INSERT

[75] Inventors: Sidney Weisman, West Caldwell; Robert F. Cotter, Sparta, both of N.J.

[73] Assignee: Howmedica, Inc., New York, N.Y.

[22] Filed: Sept. 24, 1975

[21] Appl. No.: 616,297

[52] U.S. Cl. .................. 3/1.91; 3/1.913; 128/92 C; 128/92 CA
[51] Int. Cl.[2] .......................................... A61F 1/24
[58] Field of Search ............... 3/1.9–1.913, 3/1; 128/92 C, 92 CA

[56] References Cited
UNITED STATES PATENTS

| | | | |
|---|---|---|---|
| 2,785,673 | 3/1957 | Anderson | 128/92 CA |
| 3,820,167 | 6/1974 | Sivash | 3/1.912 |
| 3,848,272 | 11/1974 | Noiles | 3/1.913 |
| 3,879,767 | 4/1975 | Stubstad | 3/1 |
| 3,938,198 | 2/1976 | Kahn et al. | 3/1.912 |

FOREIGN PATENTS OR APPLICATIONS 1,122,634  5/1956  France .................. 128/92 CA

OTHER PUBLICATIONS

Hip Prosthesis Size Definition Chart from Zimmer Catalog, Zimmer, U.S.A., Warsaw Ind., p. A3, Rev. 2, Jan., 1974, (Moore Hip Prosthesis Relied Upon).

Primary Examiner—Ronald L. Frinks
Attorney, Agent, or Firm—Connolly and Hutz

[57] ABSTRACT

A collar of a low modulus of elasticity material is interpositioned between the collar of a metal prosthetic hip stem implanted in the intermedullary canal of the femur and the adjacent calcar or outer edge of the bone. A flange depends from the insert between the upper portion of the stem and the inner wall of the bone. The interpositioned collar is either a full elongated tapered O-shape or it is open on one side of a tapered U-shape.

10 Claims, 8 Drawing Figures

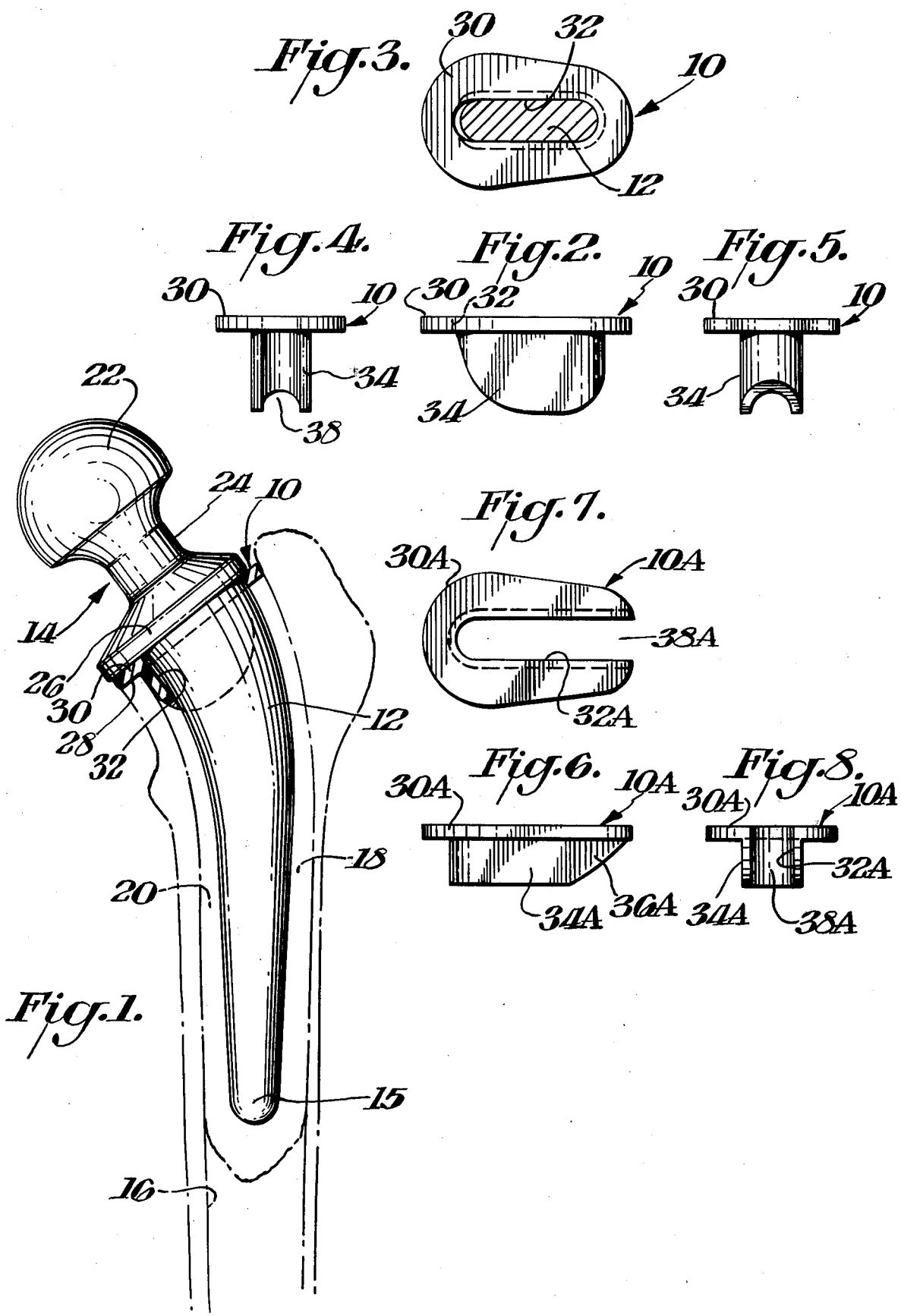

INTERPOSITIONING COLLAR FOR PROSTHETIC BONE INSERT

BACKGROUND OF THE INVENTION

The supporting collar and medial side of inserted metallic prosthesis exert pressure on the calcar of the upper portion of the femur. This results in loosening and creates a space, thus redistributing stress, such that a greater moment is created along the stem of the prosthesis, which can result in fatigue failure. An object of this invention is to provide a simple and economical means for strengthening the joint between a collar of a bone implant and the cut edge of the bone against which it bears and between the adjacent inner wall of the bone and inserted stem.

SUMMARY

In accordance with this invention an interpositioned collar of low modulus of elasticity material is interposed between the collar of the metal implant and the adjacent edge of the bone and about the adjacent portion of the stem within the inner wall of the bone. The low modulus material is, for example, ultrahigh molecular weight polyethylene. The interpositioned collar may be on elongated O-shape or open on one side in a U-shape. A short flange depends from the collar between the adjacent portion of the stem and the medial wall of the bone. The flange may be open at one side and may have a tapered profile to facilitate insertion and adjust to different spaces within the intermedullary canal.

BRIEF DESCRIPTION OF THE DRAWING

Novel features and advantages of the present invention will become apparent to one skilled in the art from a reading of the following detailed description in conjunction with the accompanying drawings wherein similar reference characters refer to similar parts and in which:

FIG. 1 is a side view in elevation of one embodiment of this invention inserted between the collar of a metal hip stem and the portion of a femur bone within which the hip stem is implanted;

FIG. 2 is a side view in elevation of the insert shown in FIG. 1;

FIG. 3 is a top plan view of the insert shown in FIG. 2 with adjacent portion of a hip stem shown in cross section;

FIG. 4 is a left side elevational view of the insert shown in FIG. 2;

FIG. 5 is a right side elevational view of the insert shown in FIG. 2;

FIG. 6 is a side view in elevation of a modified form of the insert shown in FIGS. 1-5;

FIG. 7 is a top plan view of the insert shown in FIG. 6; and

FIG. 8 is a right side view in elevation of the insert shown in FIG. 6.

DESCRIPTION OF THE PREFERRED EMBODIMENTS

In FIG. 1 is shown an interpositioning collar insert 10 surrounding the upper portion of stem 12 of metallic hip stem implant 14 inserted within the intermedullary canal 16 of femur 18 and secured therewithin by grouting cement 20, which is, for example, a methyl methacrylate bone cement. Metal hip stem 14 is, for example, made of Vitallium metal.

Vitallium is a special cobalt-chromium alloy developed and used for cast partial and full dentures, and for internal applications by surgeons. Cobalt and chromium constitute over 90% of its composition. Sp.gr. 8.29; tensile strength, 100,000–120,000 lb./sq.in.: yield point, 70,000–80,000 lb./sq.in.: Rockwell "C" hardness, 23–28; elongation, 15–20% modulus of elasticity in tension, 30,000,000–32,000,000. When polished, it is exceedingly smooth and permanently lustrous. Its outstanding qualities are permanent inertness in relation to living tissues, and high degree of resistance to corrosion. Vitallium is a metal made by Howmet Corp., Dover, N.J.

Metal hip stem 14 includes end ball 22 connected by neck 24 to collar 26. Collar insert 10 is interpositioned between metal collar 26 and adjacent bone edge or calcar 28. Collar insert 10 is made, for example, of a low modulus of elasticity material of a biocompatible nature, such as ultrahigh molecular weight polyethylene.

As shown in FIGS. 2–5, collar insert 10 includes a collar element 30 in the form of a substantially elongated tapered closed O-shape having a substantially oval central aperture 32. Short flange 34 extends in a U-shape for disposition about the upper portion of stem 12, as shown in FIG. 3.

The stem of the prosthesis is held firmly within the intermedullary canal of the bone by interpositioning a material having a relatively low modulus of elasticity than either the bone, metal or methyl methacrylate cement which is currently used as a grouting agent. The stresses ordinarily imposed upon the calcar and the medial wall of the bone are thus minimized because of the absorptive characteristics of the low modulus of elasticity plastic component which has the necessary rigidity combined with flexibility and/or resilience to absorb shocks as well as stress which are normally imposed upon the bone structure.

Collar insert 10 is made, for example, of a material which has proven successful in applications within the human body, namely, ultrahigh molecular weight polyethylene or similar plastic materials which have also been found acceptable. Its interposition between the upper portion of the prosthesis stem and the bone minimizes and/or prevents pressure upon the bone and ultimate necrosis which would produce a space which could effectively allow bending of the prosthesis stem.

In FIG. 1 is shown collar 10 made of ultrahigh molecular weight polyethylene which completely surrounds the upper portion of the stem 12 (shown in FIG. 3) just under the shoulder of the prosthesis, progressing down approximately ½ inch to 1 inch along the stem. The collar has a flange which fits under the shoulder of the prosthesis, thus redistributing the stress over a wider surface of the more compliant plastic material. In addition, the collar encircles the stem to serve as a buffer between the prosthesis and the cement and bone. The tail 15 of stem 12 (shown in FIG. 1) is similar to upper stem cross section, but smaller with a smooth taper inbetween.

In FIGS. 6–8 is shown a collar insert 10A in the shape of a "U" which has a flange 34A to fit against the underside of the collar and a projection 36A away from the flange to fit along the stem of the prosthesis. Flange 34A is open at end 38A on the lateral side. U-shaped collar element 30A is also tapered in plan view. Its open configuration facilitates installation and removal.

We claim:

1. An interpositioning collar for disposition between a metal prosthetic bone implant having a stem and adjacent portions of the bone comprising a substantially flat collar element having a substantially central hole adjacent the inner periphery of the collar through which the stem of the metal implant is inserted, a substantially short flange depending adjacent the inner periphery of the collar for disposition between the adjacent portions of the stem and bone, the interpositioning collar being resilient and having a relatively low modulus of elasticity for firmly wedging the metal implant within the bone and absorbing shocks therebetween, the collar element is substantially elongated in plan view, and the flange is substantially U-shape with an open end, and the open end being disposed adjacent one of the ends of the collar element.

2. An interpositioning collar as set forth in claim 1 wherein it is comprised of ultrahigh molecular weight polyethylene.

3. An interpositioning collar as set forth in claim 1 wherein the substantially flat collar element has a substantially closed elongated O-shape in plan view.

4. An interpositioning collar as set forth in claim 3 wherein the collar element is slightly tapered in plan view from one end to the other.

5. An interpositioning collar as set forth in claim 4 wherein the substantially flat collar has a substantially elongated U-shape with one of its short ends being open.

6. An interpositioning collar as set forth in claim 5 wherein the U-shape has an open end and is slightly tapered from one end to the other with the open end being narrower than the other.

7. An interpositioning collar as set forth in claim 1 wherein the side of the flange remote from the collar element is narrower than the side attached to the collar element whereby insertion within the wall of the bone is facilitated.

8. An interpositioning collar as set forth in claim 1 wherein the collar element is substantially tapered in plan view to have one smaller end, and the smaller end being disposed adjacent the open end of the flange.

9. An interpositioning collar for disposition between a metal prosthetic bone implant having a stem and adjacent portions of the bone comprising a substantially flat collar element having a substantially central hole adjacent the inner periphery of the collar through which the stem of the metal implant is inserted, a substantially short flange depending adjacent the inner periphery of the collar for disposition between the adjacent portions of the stem and bone, the interpositioning collar being resilient and having a relatively low modulus of elasticity for firmly wedging the metal implant within the bone and absorbing shocks therebetween, the collar element has a substantially U-shape in plan view having an open end, the flange also having a substantially U-shape with an open end, and the open end of the flange being adjacent the open end of the collar.

10. An interpositioning collar as set forth in claim 9 wherein the flange is substantially coextensive with the open end of the collar element.

* * * * *